United States Patent
Twomey et al.

(10) Patent No.: US 7,749,279 B2
(45) Date of Patent: Jul. 6, 2010

(54) BONE CEMENT PLUG

(75) Inventors: Richard Twomey, Knaresborough (GB);
Neil Watkins, Cheshire (GB); Rick Kowalski, Preston (GB); John Ewans, High Wycombe (GB)

(73) Assignee: Depuy International Ltd. (GB)

( * ) Notice: Subject to any disclaimer, the term of this patent is extended or adjusted under 35 U.S.C. 154(b) by 509 days.

(21) Appl. No.: 10/564,130

(22) PCT Filed: Dec. 5, 2003

(86) PCT No.: PCT/GB03/05324

§ 371 (c)(1),
(2), (4) Date: Aug. 8, 2006

(87) PCT Pub. No.: WO2004/052243

PCT Pub. Date: Jun. 24, 2004

(65) Prior Publication Data

US 2007/0083212 A1 Apr. 12, 2007

(30) Foreign Application Priority Data

Dec. 7, 2002 (GB) .................................. 0228575.7

(51) Int. Cl.
*A61F 2/44* (2006.01)
(52) U.S. Cl. .................................................. 623/23.48
(58) Field of Classification Search .... 623/23.47–23.63
See application file for complete search history.

(56) References Cited

U.S. PATENT DOCUMENTS

| 4,011,602 | A | * | 3/1977 | Rybicki et al. ........... 623/23.76 |
| 4,447,915 | A | * | 5/1984 | Weber .......................... 606/95 |
| 5,092,891 | A | | 3/1992 | Kummer et al. |
| 5,554,191 | A | * | 9/1996 | Lahille et al. ............ 623/17.11 |
| 5,935,169 | A | * | 8/1999 | Chan ....................... 623/23.48 |
| 5,997,580 | A | * | 12/1999 | Mastrorio et al. ........ 623/23.48 |
| 6,123,706 | A | * | 9/2000 | Lange ......................... 606/264 |
| 6,669,733 | B1 | * | 12/2003 | Spierings ................ 623/23.48 |
| 7,156,880 | B2 | * | 1/2007 | Evans et al. ............. 623/23.51 |
| 2003/0065395 | A1 | * | 4/2003 | Ralph et al. ............. 623/17.13 |

FOREIGN PATENT DOCUMENTS

| DE | 3445709 A1 | 6/1996 |
| DE | 4439049 A1 | 7/1996 |
| FR | 2708192 A | 2/1995 |
| GB | 2253564 A | 9/1992 |
| GB | 2324731 A | 11/1998 |
| WO | WO0024341 A | 5/2000 |
| WO | WO0026926 A | 5/2000 |
| WO | WO0166045 A | 9/2001 |

* cited by examiner

*Primary Examiner*—David Isabella
*Assistant Examiner*—Ann Schillinger

(57) ABSTRACT

A bone cement plug for fitting into the intramedullary canal within a bone to restrict flow of bone cement during surgery comprises a sleeve (2) whose wall is circumferentially continuous and has an outer surface (10) for contacting the wall (32) of the canal. The sleeve (2) is formed from a deformable material so that it can be expanded transversely to contact the surface (32) of the canal. The plug includes an expander which can be drawn through the cavity (12) in a direction generally along the axis of the sleeve (2), to cause the sleeve (2) to expand transversely to contact the surface (32) of the canal. The inner surfaces of the wall converge towards the end (16) of the sleeve (2) towards which the expander is drawn to cause the sleeve (2) to expand to contact the surface (32) of the canal.

17 Claims, 1 Drawing Sheet

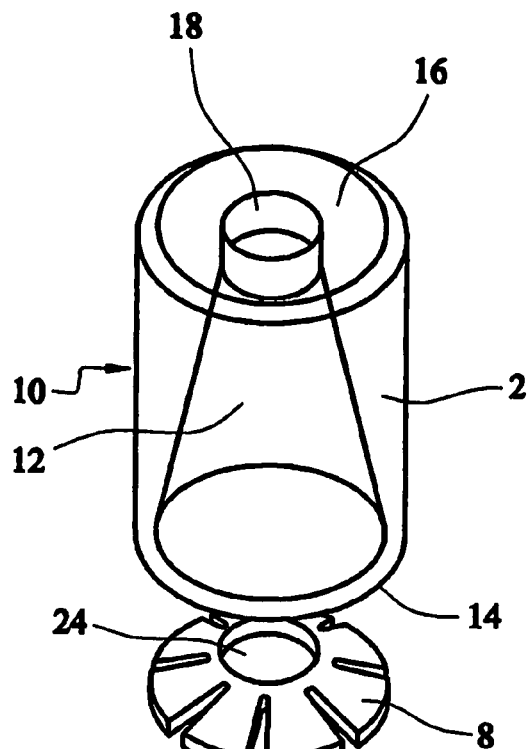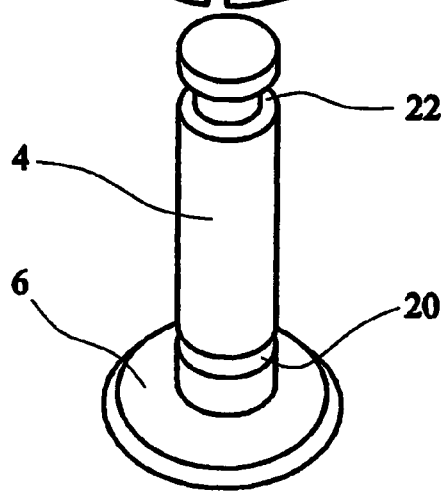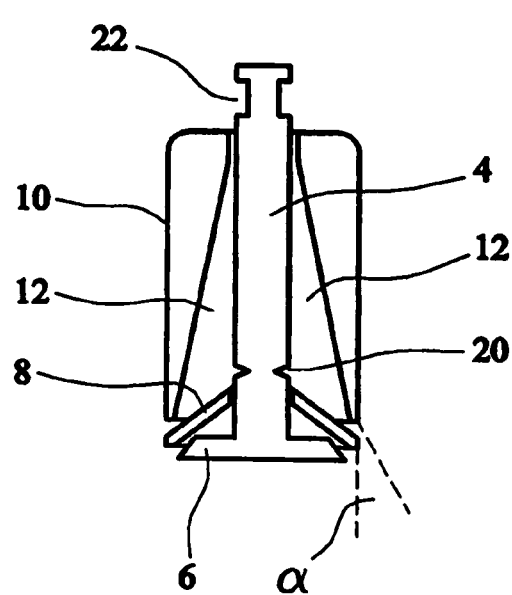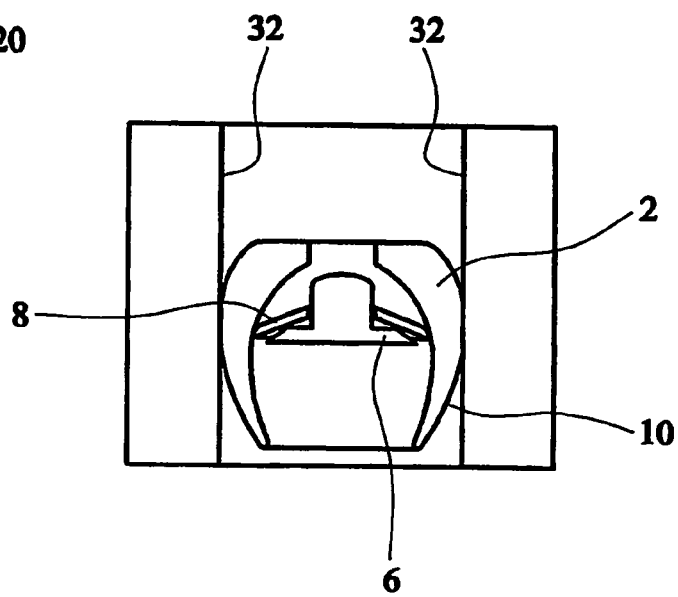
FIG. 1
FIG. 2
FIG. 3

BONE CEMENT PLUG

This invention relates to a bone cement plug for fitting into the intramedullary canal within a bone to restrict flow of bone cement during surgery.

Surgical procedures in which components of orthopaedic joint prostheses are fixed to natural bone tissue by means of curable bone cement materials are well established. Components which are to be fixed to a long bone such as the femoral component of a hip joint prosthesis or the humeral component of a shoulder joint prosthesis have a stem which is received in the intramedullary canal of the bone, which is fixed within the canal by means of bone cement. The surgical procedure generally involves injecting a quantity of bone cement into the canal prior to locating the stem of the prosthesis into the canal so as to apply pressure to the cement. The cement is then allowed to cure.

It can be important to limit the depth within the canal into which the cement penetrates, for example to minimise undesirable effects in other parts of the patient's bone structure, and also significantly to enable pressure to be applied to the cement when the prosthesis component is implanted, to encourage the cement to penetrate the wall of the bone which defines the intramedullary cavity. It is known to use a bone cement plug in order to define the distal end of the cavity into which the stem of a prosthesis component is to be implanted, to limit the depth within the canal into which cement can penetrate. The bone cement plug should engage the wall of the canal so that it is not displaced significantly when the stem of the prosthesis component is inserted into the canal. Generally, the bone cement plug is prevented from being displaced by frictional forces between it and the internal wall of the canal. Proper selection of a bone cement plug which has an appropriate size to be an interference fit in the canal is essential: if the bone cement plug is too big, either it or the bone tissue which defines the canal will be damaged, and if it is too small, it will not engage the internal wall of the cavity with sufficient security for it to be displaced when the bone cement is pressurised.

Bone cement plugs which can be expanded transversely to engage the wall of the intra-medullary canal are known. For example, a bone cement plug is disclosed in WO-00/28926 which comprises a quantity of a deformable plugging material which is located between two plates. An instrument is included by which one of the plates can be drawn towards the other plate, compressing the plugging material axially and causing its transverse dimension to increase to engage the wall of the intramedullary canal. A bone cement plug is disclosed in U.S. Pat. No. 4,447,915 which comprises a hollow outer member and a conical expander. The outer member can be expanded transversely by drawing the expander into the outer member.

It can be desirable for a bone cement plug to have a wide range of expansion so that it can be used in patient's bones with a wide range of sizes of intramedullary canal. The present invention provides a bone cement plug which comprises a hollow sleeve having a cavity within it and whose wall thickness increases towards one end, and an expander which can be drawn into the cavity, towards the end of the sleeve in a direction from the end with the smaller wall thickness towards the end with the larger wall thickness.

Accordingly, in one aspect, the invention provides a bone cement plug for fitting into the intramedullary canal within a bone to restrict flow of bone cement during surgery, which comprises:

a. a sleeve whose wall is circumferentially continuous and has an outer surface for contacting the wall of the canal, and whose inner surfaces define an internal cavity and the longitudinal axis of the sleeve, the sleeve being formed from a deformable material so that it can be expanded transversely to contact the surface of the canal, b. an expander which can be drawn through the cavity in a direction generally along the axis of the sleeve, to cause the sleeve to expand transversely to contact the surface of the canal, in which the inner surfaces of the wall converge towards the end of the sleeve towards which the expander is drawn to cause the sleeve to expand to contact the surface of the canal.

The bone cement plug of the invention has the advantage that it can be expanded to engage the internal surfaces of the intramedullary cavity within bones with a wide range of sizes, with sufficiently secure interference fits for the plug to remain approximately in place even when subjected to the pressures which can result from the insertion into the cavity of the stem of a prosthesis component. This arises from the convergence of the inner surfaces of the sleeve wall.

Preferably, the sleeve has an end wall at the end towards which the expander is drawn to cause the sleeve to expand. The end wall can be formed as a single body (usually of the same material) with the wall of the sleeve which contacts the surface of the canal when the sleeve is expanded.

Preferably, the end wall of the sleeve has an opening extending through it. Preferably, the expander comprises a shaft which extends generally along the sleeve axis, and a transverse portion which contacts the internal wall of the cavity in the sleeve, the shaft extending through the opening in the end wall of the sleeve to that it can be engaged to draw the expander through the sleeve.

Preferably, the shaft has a line of weakness at which it can be broken to allow the transverse portion of the expander to be separated from that portion of the shaft which extends through the opening in the end wall of the sleeve. It will generally be preferred that the line of weakness is positioned so that the shaft does not protrude significantly through the opening in the sleeve when the sleeve has been expanded to contact the patient's bone tissue.

Preferably, the expander includes a conical washer on the shaft which sits on the transverse portion of the expander. It is particularly preferred that the conical washer has a plurality of slots formed in it, extending partially from the outside edge of the washer towards the inside edge thereof. The slots can extend radially. The use of a conical washer has been found to increase the range of sizes to which the sleeve can be expanded. The slots allow the washer to be deformed from a conical configuration towards a flattened configuration, as the expander is drawn into the cavity within the sleeve, increasing the transverse dimension of the washer, and therefore also the effective transverse dimension of the expander.

Preferably, the shaft and transverse portion of the expander are moulded as a single component. The shaft and the transverse portion of the expander can be formed from a resorbable material, for example by moulding. The shaft and the transverse portion can be formed from a material which can be used as a bone cement, for example a polymethyl-methacrylate. The material from which the shaft and transverse portion are made should be stiffer than the material of the sleeve so that it is the sleeve which is deformed primarily when the expander is drawn into the cavity in the sleeve. The washer (when present) can be made from a material which is different from that of the shaft and the transverse portion, especially when the washer is required to deform during deformation of the sleeve.

The angle between the inner surface of the wall and the axis of the sleeve, at the end of the sleeve from which the expander is drawn through the cavity in a direction to cause the sleeve to expand transversely, will be selected so that the transverse dimension of the sleeve can be made to increase without the need to draw the expander a significant distance into the cavity within the sleeve. However, the angle should not be so great that there is significant resistance to the expander being drawn into the sleeve. Preferably, the angle between the inner surface of the wall and the axis of the sleeve, at the end of the sleeve from which the expander is drawn through the cavity in a direction to cause the sleeve to expand transversely, is at least about 20°, more preferably at least about 25°. Preferably, the angle between the inner surface of the wall and the axis of the sleeve, at the end of the sleeve from which the expander is drawn through the cavity in a direction to cause the sleeve to expand transversely, is not more than about 50°, more preferably not more than about 40°.

The outer surface of the sleeve can have surface features to promote engagement with the bone surface of the intramedullary canal. For example, the outer surface can be roughened, or it can have ridges or grooves or both on it extending in a plane generally perpendicular to the axis of the sleeve. Surface features can increase frictional forces between the sleeve and the inner surface of the intramedullary cavity.

The sleeve can have one or more indents in the surface which defines the internal cavity, extending around the cavity approximately in a plane which is perpendicular to the axis of the sleeve. Such an indent can promote engagement of the expander with the inner surface to minimise the risk of the sleeve relaxing from its expanded configuration.

The material of the sleeve should be selected having regard to its deformability. The material should be capable of being deformed by the application of moderate force to the expander. However, it has been found that materials which can be deformed too easily tend to compress in the direction in which the expander is moved in order to cause the sleeve to expand. Preferably, the hardness of the material of the sleeve is at least about 15 Shore A, more preferably at least about 20 Shore A, especially at least about 25 Shore A. Preferably, the hardness of the material of the sleeve is not more than about 75 Shore A, more preferably not more than about 55 Shore A, especially not more than about 40 Shore A. The deformability of the sleeve enables it to be expanded to fit into bone canals with a range of sizes. It can also enable it to deform to change its cross-sectional shape, for example from circular when the cross-sectional shape of the bone canal is not circular.

It can be preferred for many applications for the material of the sleeve to be resorbable. Examples of suitable resorbable materials include materials containing one or more of gelatine, glycerol, polyethylene oxide, polyethylene glycol/polybutylene terephthalate copolymer, and a foamed polylactide polymer (PLLA). Non-resorbable materials can be used such as certain elastomers. A preferred example is based on a polyurethane.

For some applications, it can be preferred for part only of the sleeve to be resorbable, for example by forming the sleeve in two or more layers of which one or more can be resorbed. In this way, partial resorption of the material of the sleeve can reduce pressure on the bone tissue which defines the intramedullary cavity. The resorbable layer can be an inner layer. Preferably, it is an outer layer.

In another aspect, the invention provides an assembly for use in orthopaedic surgery which comprises a bone cement plug as discussed above and an instrument for locating the plug in the intramedullary canal within a bone.

Preferably, the expander comprises a shaft which extends generally along the sleeve axis, and the instrument includes a socket for engaging the shaft on the expander. Preferably, the assembly includes a drive unit by which the expander can be drawn into the sleeve to cause it to expand transversely. The drive unit can be operated manually, preferably with a ratchet mechanism which allows for progressive and controlled drawing of the expander into the sleeve cavity. When the shaft has a line of weakness, continued controlled drawing the expander into sleeve cavity can lead to breakage of the shaft. The instrument for drawing the expander can be of the kind disclosed in WO-00/28926.

Embodiments of the present invention will now be described by way of example with reference to the accompanying drawings, in which:

FIG. 1 is an exploded isometric view of a bone cement plug according to the present invention.

FIG. 2 is a side elevation view, in cross-section taken on the axis of the plug, with the plug in its configuration prior to implantation in a patient's intramedullary cavity.

FIG. 3 is a side elevation view of the plug shown in FIG. 2, after it has been expanded in an intramedullary cavity to seal to the bone which defines the cavity.

Referring to the drawings, FIG. 1 shows a bone cement plug according to the present invention comprising a sleeve 2 and an expander which comprises a shaft 4, a transverse portion 6 at the base of the shaft, and a conical washer 8 which can fit over the shaft and rest against the transverse portion of the expander at the base of the shaft.

The bone cement plug is formed as a sleeve from a material which is capable of being expanded transversely. A preferred material for the expander is based on an ethylene oxide/polybutylene terephthalate copolymer. The material should be compounded so that its hardness, measured on the Shore A scale, is between about 25 and about 40.

The sleeve of the bone cement plug comprises an axially extending side wall whose outer surface 10 has an approximately constant cross-sectional shape and size. The cross-sectional shape of outer surface will generally be approximately circular. The sleeve is hollow, having a cavity 12 defined by an inner wall which converges from an open end 14 to a closed end 16. The sleeve has an end wall at the closed end, which has an opening 18 extending through it through which the shaft 4 of the expander can slide. The sleeve can be formed by techniques such as moulding and machining.

The angle α between the outer surface 10 of the sleeve and the inner wall which defines the cavity 12 is about 30°.

The expander comprises a shaft 4 and a transverse portion 6 at the base of the shaft. The shaft and the transverse portion are formed as a single part by an injection moulding process. It is generally preferred that they are formed from a material which can be used as a bone cement, such as cured polymethylmethacrylate. The shaft has a line of weakness formed in it, close to its base, provided by a groove 20. The shaft has a recess 22 close to the end opposite the base, by which the shaft can be engaged by an instrument for locating the plug in an intramedullary canal.

The expander includes a conical washer 8 which has an opening 24 extending through it through which the shaft can extend so that the washer sits against the transverse portion 6 of the expander. The washer has a plurality of slots formed in it, extending radially from the outer edge of the washer towards its centre. The slots enable the washer to be deformed from its conical configuration towards a flattened configuration so that the diameter of the washer increases. The diameter of the washer prior to it being deformed is about the same as the diameter of the transverse portion of the expander. Once it has been deformed, the diameter of the washer is greater than the diameter of the transverse portion of the expander.

A bone is prepared to receive the bone cement plug by appropriate resection of the diseased or otherwise damaged tissue. The exposed intramedullary cavity is prepared using appropriate cutting tools such as reamers and broaches, so that the cavity in the region in which the stem of a prosthesis component is to extend is defined by cancellous tissue, and so that the cross-section of the canal is circular or close to circular.

The bone cement plug, when prepared for implantation in a bone canal, is assembled as shown in FIG. 2, and is fitted to an instrument (not shown) which has a socket in which the shaft can be received. The shaft can be releasably engaged against axial separation by means of grippers which fit into the recess 22 in the shaft. The conical washer 8 is fitted on to the shaft with the shaft extending through the opening 24, so that it rests on the transverse portion 6 of the expander. In the configuration prior to use, the diameter of the washer is about the same as that of the transverse portion, and also about the same as the inner diameter of the cavity 12 at the open end thereof.

The instrument is used to insert the bone cement plug into the prepared canal at the appropriate depth so that the stem of the prosthesis component can fit into the canal. The instrument is then actuated to draw the expander through the sleeve 2, relying on the engagement between grip means on the instrument and the recess on the shaft. This causes the transverse portion 2 of the expander and the washer 8 to be drawn into the cavity 12 within the sleeve. The reducing diameter of the cavity and the action of the transverse portion against it, causes the sleeve to be deformed outwardly, to engage the inner surface 32 of the bone canal. Continued drawing of the expander into the sleeve causes the washer to flatten, so that its diameter increases as shown in FIG. 3.

When the force required to deform the sleeve on continued displacement of the expander through the cavity, reaches a certain level, it causes the shaft to break at the line of weakness provided by the groove 20. The shaft can be configured so that it breaks under a predetermined axial load. The shaft can then be removed from within the bone canal. The expanded sleeve remains within the canal, with the transverse portion of the expander and the washer within it. The short portion of the shaft above the transverse portion is located wholly within the sleeve (as shown in FIG. 3), or protrudes from the sleeve for only a short distance. The implanted plug can then provide an end stop to restrict the portion of the canal in which bone cement can be injected, and can withstand pressurisation of the cement, for example when the stem of the prosthesis component is implanted. The seal is provided between the sleeve and the walls of the canal, and also by the transverse portion of the expander and the washer which substantially prevent flow of bone cement past the sleeve through the opening 24.

Examples of dimensions (in millimetres) of bone cement plugs according to the invention are as follows:

| Dimension | Example 1 | Example 2 | Example 3 |
|---|---|---|---|
| Overall length of sleeve (2) | 9.5 | 13.0 | 17.5 |
| Diameter of sleeve (2) | 7.9 | 10.7 | 14.5 |
| Diameter of opening(18) in sleeve | 3.5 | 3.5 | 3.5 |
| Wall thickness of sleeve at open end (14) | 0.5 | 0.5 | 0.5 |
| Wall thickness of sleeve at closed end (16) | 2.2 | 3.6 | 5.5 |
| Length of shaft (4) | 17.0 | 21.0 | 27.0 |

-continued

| Dimension | Example 1 | Example 2 | Example 3 |
|---|---|---|---|
| Diameter of transverse portion (6) | 7.2 | 9.8 | 13.2 |
| Diameter of conical washer - undeformed (8) | 7.2 | 9.8 | 13.2 |
| Height of conical washer - undeformed | 3.4 | 5.6 | 8.6 |
| Minimum diameter of bone canal | 8.0 | 10.9 | 14.7 |
| Maximum diameter of bone canal | 10.9 | 14.7 | 20.0 |

The invention claimed is:

1. A bone cement plug for fitting into the intramedullary canal within a bone to restrict flow of bone cement during surgery, comprising:

a sleeve having a longitudinal axis, an outer surface configured to contact the wall of the canal, and inner surfaces configured to define an internal cavity whose diameter decreases from a distal end to a proximal end, whereat the internal cavity communicates with an opening formed in the outer surface, the sleeve being formed from a deformable material and configured to be expanded transversely to contact the surface of the canal;

an expander comprising a shaft having a distal end and a transverse portion that extends radially from the distal end of the shaft, the shaft dimensioned to extend through the opening; and a washer disposed on the shaft, and having a plurality of radially slots formed therein extending from the outside edge of the washer toward the inside edge thereof; and wherein the expander is movable within the cavity in a direction generally along the longitudinal axis from a distal position to a proximal position, whereat the washer contacts the internal cavity to cause the wall of the sleeve to expand transversely to contact the surface of the canal, wherein the transverse portion of the expander has a diameter, the washer has a first configuration, where the diameter of the washer is approximately equal to the diameter of the transverse portion, and a second configuration, where the diameter of the washer is greater than the transverse portion, and wherein when the expander is at the distal position, the washer is in the first configuration, and when the expander is in the proximal position, the washer is in the second configuration such that the outer perimeter of the washer contacts the internal cavity to cause the wall of the sleeve to expand transversely to contact the surface of the canal.

2. The bone cement plug of claim 1, wherein the sleeve has an end wall at the proximal end thereof and is formed as a single body with the wall of the sleeve.

3. The bone cement plug of claim 1, wherein the shaft is configured to be frangible at a defined line of weakness.

4. The bone cement plug of claim 1, wherein the shaft and transverse portion of the expander are formed as a single component.

5. The bone cement plug of claim 4, wherein the shaft and the transverse portion of the expander are formed from a resorbable material.

6. The bone cement plug of claim 1, wherein the angle between the inner surface of the wall and the longitudinal axis at the distal end of the sleeve is at least about 20 degrees.

7. The bone cement plug of claim 1, wherein the angle between the inner surface of the wall and the longitudinal axis at the distal end of the sleeve is not more than about 50 degrees.

8. The bone cement plug of claim 1, wherein the outer surface of the sleeve has surface features to promote engagement with the bone surface of the intramedullary canal.

9. The bone cement plug of claim 1, wherein the sleeve has at least one indent in the surface which defines the internal cavity, the indent extending around the internal cavity approximately in a plane that is perpendicular to the axis of the sleeve.

10. The bone cement plug of claim 1, wherein the hardness of the material of the sleeve is at least about 30 Shore A.

11. The bone cement plug of claim 1, wherein the hardness of the material of the sleeve is not more than about 75 Shore A.

12. The bone cement plug of claim 1, wherein the sleeve is formed from a resorbable material.

13. An assembly for use in orthopaedic surgery, comprising: a bone cement plug of claim 1 and an instrument for locating the plug in the intramedullary canal within a bone.

14. The assembly of claim 13, wherein the expander comprises a shaft that extends generally along the longitudinal axis, and wherein the instrument includes a socket for engaging the shaft on the expander.

15. The assembly of claim 13, which includes a drive unit by which the expander can be drawn into the sleeve to cause the expander to move from the distal position to the proximal position.

16. The bone cement plug of claim 1, wherein the transverse portion of the expander has a diameter, the washer has a conical configuration, where the diameter of the washer is approximately equal to the diameter of the transverse portion, and a flattened configuration, where the diameter of the washer is greater than the transverse portion, and wherein when the expander is at the distal position, the washer is in the conical configuration, and when the expander is in the proximal position, the washer is in the flattened configuration such that the outer perimeter of the washer contacts the internal cavity to cause the wall of the sleeve to expand transversely to contact the surface of the canal.

17. A bone cement plug for fitting into the intramedullary canal within a bone to restrict flow of bone cement during surgery, comprising:
- a sleeve having an outer surface configured to contact the wall of the canal, an internal cavity and being formed from a deformable material;
- an expander comprising a shaft having a distal end and a transverse portion that extends radially from the distal end of the shaft, the transverse portion having a diameter; and
- a washer disposed on the shaft, and having a plurality of radially slots formed therein extending from the outside edge of the washer toward the inside edge thereof, the washer having a conical configuration, where the diameter of the washer is approximately equal to the diameter of the transverse portion, and a flattened configuration, where the diameter of the washer is greater than the transverse portion,
- wherein the expander is movable within the cavity from a distal position, whereat the washer is in the conical configuration, to a proximal position, whereat the washer is in the flattened configuration and the outer perimeter of the washer contacts the internal cavity to cause the wall of the sleeve to expand transversely to contact the surface of the canal.

* * * * *